Figure 1:
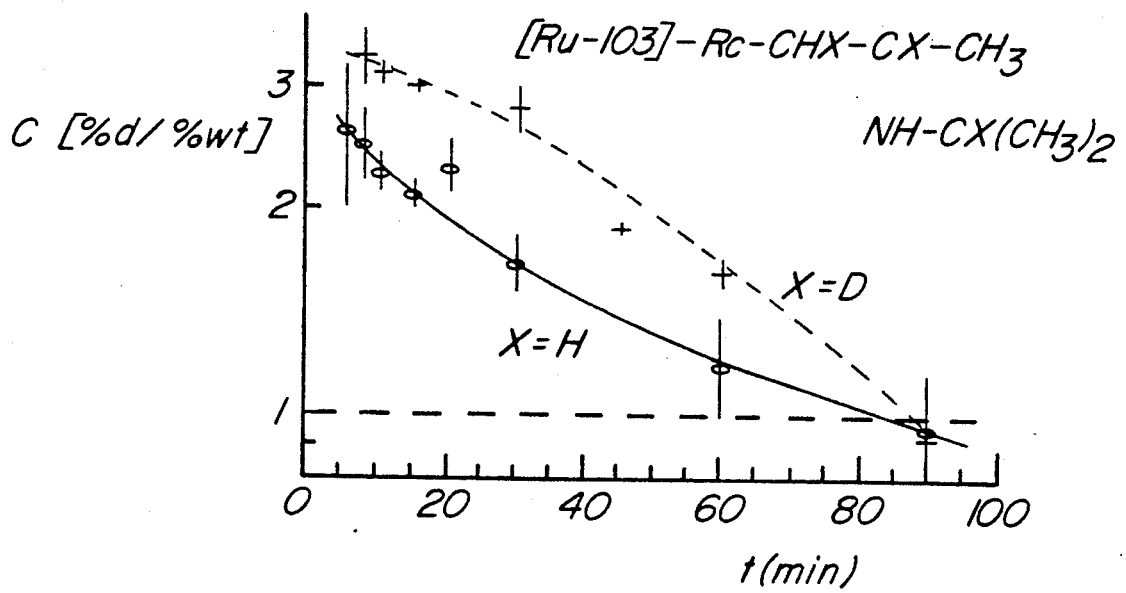

United States Patent [19]

Wenzel

[11] Patent Number: 5,167,948
[45] Date of Patent: Dec. 1, 1992

[54] DIAGNOSTIC OR RADIOTHERAPEUTIC COMPOSITION COMPRISING A HYDROGEN CONTAINING COMPOUND

[75] Inventor: Martin Wenzel, Berlin, Fed. Rep. of Germany

[73] Assignee: Mallinckrodt Medical, Inc., St. Louis, Mo.

[21] Appl. No.: 455,432

[22] PCT Filed: Jul. 8, 1988

[86] PCT No.: PCT/NL88/00033
§ 371 Date: Nov. 21, 1989
§ 102(e) Date: Nov. 21, 1989

[87] PCT Pub. No.: WO89/01342
PCT Pub. Date: Feb. 23, 1989

[30] Foreign Application Priority Data
Aug. 7, 1987 [EP] European Pat. Off. ........ 87201506.0

[51] Int. Cl.$^5$ .................................... A61K 49/02
[52] U.S. Cl. ..................... 424/1.1; 534/10; 534/14
[58] Field of Search .............. 424/1.1; 534/10, 14

[56] References Cited

PUBLICATIONS

Matalon, R. et al. "The use of deuterated phenylalanine . . . in children", *J. Inher. Metab. Dis.*, 1982, 5(1), pp. 17-19 [CA. 96:212975d].

Schneider, M. et al. "Labeling of acetylruthenocene . . . or tritium", *J. Lab. Compd. Radio.*, 1982, 19(5), pp. 625-629 [CA. 97:127792t].

Dyck, L. et al., "Effects of Deuterium Substitution . . . Vivo Study", *J. Neuro.*, Feb. 1986, 46(2), pp. 399-404.

Wenzel et al. "Verbesserte Diagnostik durch deuterierte Radiopharmaka?", *Appl. Radiat. Isot.* 39, 10, 1988 (Wenzel I).

Wenzel et al. "Synthesis of Ferrocene-resp. Ruthenocene Amphetamines", *Jr. Labelled Compds. and Radioph.* XXV, 2, p. 121, 1988 (Wenzel II).

*Primary Examiner*—Robert L. Stoll
*Assistant Examiner*—C. Sayala
*Attorney, Agent, or Firm*—Evan R. Witt

[57] ABSTRACT

The invention relates to a diagnostic or radiotherapeutic composition, comprising a hydrogen containing compound in addition to a pharmaceutically acceptable formulation means and optionally an inactive carrier and/or one or more auxiliary substances, wherein the hydrogen containing compound comprises at least one deuterium atom. The invention further relates to a compound to be used for said composition and to a kit for preparing a radio-diagnostic composition.

11 Claims, 3 Drawing Sheets

DIAGNOSTIC OR RADIOTHERAPEUTIC COMPOSITION COMPRISING A HYDROGEN CONTAINING COMPOUND

The invention relates to a diagnostic or radiotherapeutic composition comprising a hydrogen containing compound. The invention further relates to a compound to be used for said composition and to a kit for preparing a radiodiagnostic composition.

Frequently used diagnostic compositions comprise radionuclide-labelled compounds. Such compounds are used for diagnostic examination e.g. into deviations in shape and function of internal organs and into the presence and location of pathological processes in the body. For this purpose, a composition in which the radioactive compound is present is administered to the patient, for example, in the form of an injectable liquid. By means of a suitable detector, e.g. a gamma camera, images can be obtained by recording the emitted radiation of, for example, the organ or the pathological process in which the radioactive compound has been incorporated.

Another important tool in medical diagnostics is NMR imaging. In this technic generally diagnostic compositions are used comprising NMR contrast agents. These contrast agents cause an image producing or contrast intensifying effect in the organ or tissue wherein they are incorporated, thus allowing the obtainment of images by using suitable detection apparatus.

Radiotherapeutic compositions are injectable compositions comprising a radioactive compound for radiotherapeutic application. It is in the purpose of this radioactive compound to emit a suitable radiation, preferably beta-rays after incorporation in the target organ or tissue, generally a malignant tumour. By this irradiation the tumour can be eliminated or its growth can be prevented.

The above radioactive compounds or agents have one characteristic in common in that they are administered in very low dosages to achieve the desired purpose, viz. to enable a diagnostic examination or to irradiate the target organ or tissue without causing adverse side-effects. Administration of radiodiagnostic agents in larger quantities than the minimal dosages needed for imaging enhances the risk of accumulation of these agents in other places of the body than in the target organ or tissue, as a consequence of which the concentration of the agent in the environment of said target organ or tissue is increased. These background disturbances may have a serious impact on the examination of the target organ or tissue due to a decreased contrast between target organ and environmental tissue. In addition, when using radionuclide-labelled compounds, accumulation of radioactivity in other organs and tissues than the organ or tissue to be examined constitutes an extra radiation burden for these other organs and tissues which may adversely influence their health and proper functioning. This last-mentioned problem applies even more strongly to radiotherapeutic compounds, which compounds are only intended to be vehicles for carrying the radiation dose to the target organ or tissue, in particular a malignant tumour. In addition, diagnostic agents which are in particular intended to give information on the functioning of body organs should be administered in dosages which are as small as possible to not disturb endogenic biochemical processes or equilibriums in the body.

It will be evident from the above explanation that in particular the "target organ specificity" is of utmost importance for the above compounds or agents to be used in diagnostic or radiotherapeutic compositions. By the term "target organ specificity" is to be understood the presence of the compound in question in the target organ or tissue selectively (i.e. compared to other organs or tissues, like blood and muscles) during a predetermined well-defined period of time. This latter requirement means that the compound is carried along to and accumulated in the target organ or tissue sufficiently fast and that its residence time in said organ or tissue is sufficiently long to allow a diagnostic examination or, for a radiotherapeutic compound, to make an optimum use of its radiation potential.

The "target organ specificity" of many known diagnostic and radiotherapeutic compounds leaves much to be desired. For example, a compound may remain too long in the body after its action has been finished or the examination has been performed, and thus contribute an unnecessary burden for the patient. On the contrary, a compound may leave the body too fast to do its job in a proper way. An insufficient "target organ specificity" is especially considered as a disadvantage if the compounds are intended to be used for function examination and radiotherapy.

It is the object of the invention to provide a diagnostic or radiotherapeutic composition comprising a hydrogen containing compound having an improved "target organ specificity". It has been found that this object can be achieved by means of a diagnostic or radiotherapeutic composition comprising a hydrogen containing compound in addition to a pharmaceutically acceptable formulation means and optionally an inactive carrier and/or one or more auxiliary substances, which composition, according to the present invention, comprises as the hydrogen containing compound a compound having at least one deuterium atom.

From a publication of Foster in Advances in Drug Research 14, 2-36(1985) it is known to use deuterium labelling of drugs to study deuterium isotope effects in the metabolism of these drugs in concentrations usually applied for chemotherapy with these drugs. Dyck et al have disclosed in J. Neurochem. 46, No. 2, 399–404 (1986) the effects of deuterium substitution on the catabolism of $\beta$-phenylethylamine. The authors draw the conclusion that deuterium substitution seems to be a useful strategy to enhance the pharmacological effects of a compound without significantly altering its basic chemical structure. It was the intention of the authors to compare the neurochemical effects of deuterium substitution on a behaviourally effective dose of $\beta$-phenylethylamine. In such high doses they indeed demonstrated, that deuteration increased the amounts of $\beta$-phenylethylamine found in that brains, plasma and liver of the test animals, probably due to slower metabolization.

The diagnostic compounds to be used in the compositions of the present invention, however, do not have a therapeutic effect as is intended for the above described $\beta$-phenylethylamine. On the contrary, any pharmacological activity is highly undesired. As mentioned before, radiodiagnostic compounds or agents should only carry the radioactivity to the target organ or tissue selectively, and therefore should be administered in very small quantities to accomplish this task properly.

The same holds for radiotherapeutic compounds, which only act as vehicles for carrying the radiation dose to the target organ or tissue. Therefore diagnostic compounds cannot be used in pharmacologically effective doses. It was the intention of Dyck et al to improve the effectivity of a therapeutic compound and they have succeeded in deuterating the compound: "Such large effects may be useful in developing more potent centrally acting drugs". It is the object of the present invention, however, to provide a diagnostic or radiotherapeutic composition showing an improved "target organ specificity" and definitely not an improved pharmacological activity. The fundamental difference between a deuterated therapeutic compound as described by Dyck et al and the subject of the present invention can best be illustrated by comparing the results described in the Dyck et al publication with the results obtained according to Examples XII-XIV, wherein radiodiagnostic compounds on the basis of aromatic substances having also an aminoethyl side chain are used. Whereas Dyck et al found an increased concentration of the deuterated compound compared to the non-deuterated compound both in the brains and in the blood, the administration of a deuterated radiodiagnostic compound in a required small dose causes, on the contrary, an increased uptake in the target organ, viz. the brains, attended with a decreased uptake in the blood, so an improved contrast between target organ and environmental tissue.

In U.S. Pat. No. 4,223,004 drug compositions are disclosed comprising a predetermined weight of a certain drug together with a predetermined proportion by weight of an isotopically distinct analogue of said drug, e.g. a deuterated analogue. Such drug compositions can be used for metabolic investigations. Similar investigations have been carried out by Matalon et al: Chem. Abstr. 1982, 96, 212975d. Schneider et al (J. Labelled Compds. Radio-pharm. 1982, 19 (5), 625–29) have labelled a ruthenocene derivative with radioactive ruthenium, deuterium or tritium, to investigate the metabolic stability of this compound. It should be emphasized, that neither in said last publication nor in the other above publications a compound is disclosed which is both deuterated and radioactively labelled in one and the same molecule, the latter modification being a necessary characteristic of radiodiagnostics.

From the above U.S. Pat. No. 4,223,004 it is clear, that upon using deuterated drugs in quantities suitable for the intended analytical purposes, i.e. in tracer amounts, the isotopiqally distinct analogue has a substantially identical metabolic behaviour compared with the unmodified drug, or, in other words the isotopically distinct analogue and the unmodified drug are absorbed, distributed and excreted through the metabolism in the same proportions. This is affirmed by the experimental results disclosed in said U.S patent specification, wherein methadone is compared with methadone-$d_3$ in man. In the light of the above disclosure it is therefore quite a surprise, that upon using a diagnostic or radiotherapeutic composition according to the invention, viz. a composition comprising as the diagnostically or radiotherapeutically significant compound a deuterated compound, in the required very low dosage of the said compound a so considerably improved "target organ specificity" is obtained.

As mentioned above, the invention also relates to diagnostic compositions to be used in NMR imaging. The NMR imaging technique is based upon the NMR signal of the protons in the tissues of the patient's body so substantially of the water protons. To intensify the image contrast one generally administers to the patients compositions comprising paramagnetic substances that change the relaxivity of the protons in the tissue. Examples of such paramagnetic substances are complexes of paramagnetic ions of e.g. iron, manganese or gadolinium, or organic paramagnetic substances as nitroxyles. Generally the toxicity of the contrast agents is a serious problem and a great number of investigators is occupied in searching for new compounds having either a decreased toxicity or a stronger influence on the relaxivity of the protons in the tissue. It is indeed a great surprise, that contrast agents wherein at least one hydrogen atom is substituted by deuterium have an improved influence on the relaxivity of the protons, as will be apparent from the examples. Consequently in a diagnostic composition of the invention the contrast agent comprising at least one deuterium atom can be administered in a substantially lower dose to the patient to reach the same effect as a non-deuterated compound, so that the burden for the patient is decreased.

J. C. Gore has investigated the physical factors in designing contrast agents for NMR imaging: IEEF Engineering in Medicine and Biology, 4, 1985 (Sep.), No 3, pp. 39–42). The author suggests some alternatives to the use of paramagnetic metal ions. In this connection he suggests the use of non-hydrogenous bulk fluids, e.g. deuterated bulk fluids, to alter the relaxation behaviour. However, as will be clear from Example IX of the present application, substitution of $H_2O$ by $D_2O$ as a bulk fluid does not change the relaxation time significantly.

For quite a different purpose as the purpose of the invention beta-diketones have been modified by deuteration and used as NMR shift reactants: French patent application 2159411. Such deuterated compounds cannot disturb with their own proton signals the proton signals of the substance to be analyzed by NMR, because they are transparant in said analysis.

A suitable NMR contrast agent to be used in a diagnostic composition according to the invention is a substance selected from the group consisting of metal complexes of unsubstituted or substituted cyclopentadienyl and metals of the 7th or 8th subgroup metal chelates of $C_2$-$C_5$ alkylene di- or polyamineacetic acids and lanthanides or their salts, nitroxyles, and aminoxides, which substance comprises at least one deuterium atom. If the above cyclopentadienyl group is substituted, said cyclopentadienyl group may be substituted with one or more side chain groups selected from $C_1$-$C_4$ alkyl $C_1$-$C_4$ alkoxy and $C_2$-$C_5$ alkoxycarbonyl. It has been found that an NMR contrast agent having a considerably improved influence on the protons relaxivity is a substance selected from the group consisting of (a) a ferricinium compound that is unsubstituted or substituted with at least one side chain group as defined above, wherein at least one hydrogen atom of the ferrocene ring system and/or at least one hydrogen atom of the side chain group, if present, is substituted by deuterium, and (b) a chelate of gadolinium and a $C_2$-$C_5$ alkylene di- or polyamineacetic acid of which at least one C—H bond is substituted by a C—D bond. It has been found that this deuterium effect occurs at all paramagnetic substances that have deuterium directly incorporated in the molecule. The addition of deuterium solely, i.e. separated from paramagnetic molecules, e.g. as $D_2O$, is not effective, as will become apparent from the examples.

A suitable radiotherapeutic composition according to the invention comprises as the active ingredient a compound carrying a radionuclide suitable for radiotherapy, said compound comprising at least one deuterium atom. If said compound is a high-molecular compound such a compound is preferably selected from the group consisting of proteins, like monoclonals, and proteinaceous substances. If said compound is a low-molecular compound such a compound is preferably selected from the group of guanidine derivatives, e.g. meta-iodobenzylguanidine, bleomycins and aliphatic phosphonates like hydroxyethylene diphosphonate, methylene diphosphonate or hydroxymethylene diphosphonate. Suitable radionuclides for radiotherapy are alpha- or beta-emitters e.g. the radionuclides listed in "Radionuclides for Therapy" ed. by P. A. Schubiger and P. H. Hasler, Jun. 13–14, 1986. Such radionuclides are preferably selected from the group consisting of I-131, Re-186, Re-188, Cu-67, Pb-212, Bi-212, As-77, Y-90, Ag-111 and Pd-109.

As a radiodiagnostic composition is to be preferred a composition comprising as the radiolabelled compound a compound comprising at least one deuterium atom (deuterated compound) and selected from the group consisting of radiolabelled N-alkylaminoalkylaryl compounds, radiolabelled metallocenyl compounds, radiolabelled fatty acids or derivatives thereof, radiolabelled carbohydrates or derivatives thereof, radiolabelled proteins or proteinaceous substances, radiolabelled peptides, e.g. amino acids di-, tri- or polypeptides, or derivatives thereof, metal radionuclides chelated with alkyleneamine oximes or their derivatives, metal radionuclides chelated with substituted or unsubstituted alkyl isocyanides or derivatives thereof, radiolabelled receptor binding substances, e.g. dopamine receptors such as certain spiro compounds like iodospiperidol and the N-methylderivative thereof and boronic acid adducts of metal radionuclides chelated with oximes.

The alkyl groups in the N-alkylaminoalkylaryl compounds, mentioned above, have preferably 1 to 6 carbon atoms; the aryl group is preferably an unsubstituted phenyl group or a phenyl group substituted with $C_1$–$C_4$ alkyl or $C_1$–$C_4$ alkoxy.

The radiolabelled metallocenyl compounds mentioned above also include the compounds disclosed in European patent application 113135 and can preferably be represented by the general formula

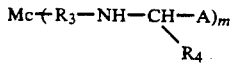

wherein
Mc is a metallocenyl group with a radioactive central atom selected from radionuclides of the following metals: iron, ruthenium, osmium, chromium, vanadium, cobalt and rhodium;
$R_3$ is a carbonyl group or a $C_1$–$C_4$ alkylene group, which alkylene group is optionally substituted with $C_1$–$C_4$ alkyl;
$R_4$ is a hydrogen atom or a $C_1$–$C_4$ alkyl group;
A is a hydrogen atom, a $C_1$–$C_4$ alkyl group, a carboxy group or a salt thereof, a $C_2$–$C_5$ alkoxycarbonyl group, or a $C_2$–$C_5$ alkanoyl group; and
m is 1–4.

Preferred examples of radiolabelled fatty acids or derivatives thereof are ω-radioactive halogen-substituted phenyl fatty acids or pharmaceutically acceptable salts thereof, in which fatty acids the alkyl chains may be interrupted with S or Se and may be substituted, if desired, with $C_1$–$C_4$ alkyl, phenyl or substituted phenyl.

Radiolabelled proteins or proteinaceous substances include metal-radionuclide labelled monoclonal antibodies and antibody fragments, wherein the protein or the complex forming coupling agent is deuterated.

Preferred radiolabelled tripeptides are the technetium-99m chelates disclosed in European patent applications 173424 and 250013 presented by the general formula

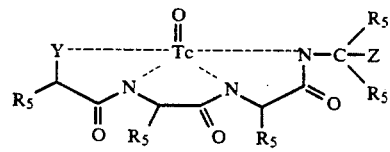

wherein
Tc represents technetium-99m,
Y is S or NH,
each $R_5$ may be independently H or $C_1$–$C_2$ alkyl, and
Z is H, $CO_2H$, $CONH_2$, $CO_2$-($C_1$–$C_4$)alkyl, $SO_3H$, $SO_2NH_2$ or $CONHCH_2CO_2H$.

Examples of radiolabelled carbohydrates are radioactive halogen substituted monosaccharides, like 18° F.-fluorodesoxyglucose and phenyl-monosaccharides and derivatives thereof.

Suitable examples of oximes are alkylene dioximes like glyoxime.

Preferred radiolabelled isocyanides include $C_2$–$C_6$ alkylisocyanides, like tert.-butyl isocyanide, labelled with suitable metal-radionuclides preferably technetium-99m.

A suitable composition, especially for brain imaging, is a composition comprising as the radiolabelled compound a compound of the general formula

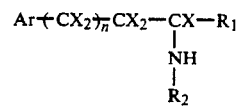

wherein
Ar is a radioactive halogen-labelled phenyl group or a metallocenoyl group radiolabelled with ruthenium 95 or ruthenium 97,
$R_1$ is a $C_1$–$C_4$ alkyl group
$R_2$ is a $C_1$–$C_6$ alkyl group of which the hydrogen atom or atoms may be deuterated,
X is completely or partly deuterated hydrogen, and
n is 0 or 1.

These radiodiagnostic compositions can be used conveniently in a method of subjecting a warm-blooded living being to a radioassay, using a technique of external imaging, to detect the radioactivity accumulated at the location of the target organ or tissue. The invention therefore also relates to a method of subjecting a warm-blooded living being, in particular a human being, to a radioassay, wherein said composition, if desired after dilution with a pharmaceutically acceptable liquid, is administered to the being, the quantity of administered radioactivity being sufficient for detection by means of external imaging, after which the being is subjected to external imaging to detect accumulated radioactivity and to thus determine the location thereof in the body of the being. The quantity of the administered imaging active substance may be very small, but, of course, must be sufficient to enable detection by external imaging. A quantity of approximately 0.1 to 10 mCi of radioactive material, for example 0.5 to 3 mCi, per 70 kg of body weight has proved suitable for this purpose.

The invention further relates to new deuterated compounds to be used in the compositions according to the invention mentioned above. Such new compounds include NMR and rontgen contrast agents selected from the group consisting of (a) a metal complex of cyclopentadienyl, that is unsubstituted or substituted with at least one side chain group, selected from $C_1$-$C_4$ alkyl, $C_1$-$C_4$ alkoxy and $C_2$-$C_5$ alkoxycarbonyl, and a metal of the 7th or 8th subgroup, preferably ferrocene, ruthenocene or their derivatives or salts, wherein at least one cyclopentadienyl hydrogen atom and/or side chain group hydrogen, if present, is substituted by deuterium, and (b) a metal chelate of a lanthanide or its salt and a $C_2$-$C_5$ alkylene di or polyamineacetic acid, wherein at least one C-H bond is substituted by a C-D bond.

Other new deuterated compounds according to the invention which can be used in radiodiagnostic compositions are radiolabelled deuterated compounds selected from the group consisting of radiolabelled N-alkylaminoalkylaryl compounds, radiolabelled metallocenyl compounds radiolabelled fatty acids or derivatives thereof radiolabelled carbohydrates or derivatives thereof, radiolabelled proteins or proteinaceous substances, radiolabelled peptides, e.g. amino acids, di-, tri- or polypeptides, or derivatives thereof, metal-radionuclides chelated with alkyleneamine oximes or their derivatives, metal-radionuclides chelated with substituted or unsubstituted alkyl isocyanides or derivatives thereof and boronic acid adducts of metal-radionuclides chelated with oximes, wherein the radiolabel is preferably selected from radioactive halogen or from a metal-radionuclide, and wherein the metal-radionuclide is preferably selected from the group consisting of Tc-99m, Pb-203, Ga-67, Ga-68, As-72 In-111, In-113m and Ru-97.

Preferred radiolabelled deuterated compounds are described hereinbefore.

Especially suitable for use in a radiodiagnostic composition has proven to be a compound having the general formula

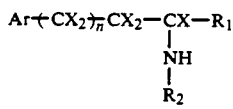

wherein the symbols have the meanings mentioned hereinbefore.

The desired deuterated compounds can be prepared in a manner known per se for the preparation of related compounds. So deuterated compounds can be prepared conveniently by a reaction between two starting compounds, one of which is deuterated, or by an oxidation reaction, reduction reaction, alkylation reaction or hydrolysis, wherein a deuterated oxidating agent, a deuterated reducing agent, a deuterated alkylating agent or a deuterated hydrolysation agent is used. Suitable deuteration agents are $D_2O$, $LiAlD_4$, $CD_3I$ and other deuterated alkylhalides, $NaBD_4$, $Na[BCND_3]$, deteurium gas and other deuterated reducing agents. Deuterated proteins or proteinaceous substances are preferably prepared by a biosynthesis in $D_2O$. Also the radiolabelled deuterated compounds mentioned above can be prepared in a manner known per se for the preparation of related compounds. So the new radiolabelled compounds are preferably prepared by reacting the corresponding non-radiolabelled deuterated compound, obtained as indicated above, with a suitable radiolabelling agent, preferably an agent selected from the group consisting of water-soluble compounds or compounds injectable in a suitable formulation, e.g. emulsions, colloids or liposomes, labelled with the desired radionuclide. Such labelling agents are preferably selected from a water-soluble compound of a radioactive halogen or a salt or chelate of a metal-radionuclide, selected from the group consisting of Tc-99m, Pb-203, Ga-67, Ga-68, As-72, In-111, In-113m and Ru-97.

Finally the invention relates to a kit for preparing a radiodiagnostic composition according to the invention. Such a kit enables the user to carry out the above process for preparing the radiolabelled compound by himself prior to using the composition for a radioassay. Said kit comprises the non-radiolabelled deuterated compound defined above, and, if desired, a reducing agent, one or more formulation agents and/or auxiliary substances, to which a solution of the desired radionuclide, in particular Tc-99m, available as pertechnetate from a Mo-Tc generator, should be added, and, if desired, instructions for use with a prescription for carrying out the desired process. In a suitable embodiment such a kit comprises as the non-radiolabelled compound a deuterated $C_2$-$C_8$ alkylisocyanide, preferably deuterated t.-butylisocyanide. This principle is also applicable for the easy preparation of radiotherapeutical compositions via similar kit formulations.

The invention will now be described in greater detail with reference to the ensuing specific examples.

EXAMPLE I

Preparation of 1-ferrocenyl-2-aminoethane-1,2-$d_2$
(deuterated ferrocenyl-ethylamine)

1-Ferrocenyl-2-nitro-ethylene is dissolved in dry diethylether and then reduced with an excess of $LiAlD_4$. After the reduction has been finished the $LiAlD_4$ is inactivated with aqueous ethanol, sucked off and washed with dry diethylether. The desired product is crystallized as the succinate with succinic acid from toluene/ethanol as the solvent and is obtained in a yield of 40%. TLC: diethylether/diethylamine (95/5): $R_f$ 0.16. $^1$H-NMR 250 MHz in $CDCl_3$: Fc-d=4.13 ppm; -$NH_2$-d=2.18 ppm; -CHD-d=2.51 ppm.

In case the starting nitro compound is converted with $D_2O$ under alkaline conditions prior to the above reduction reaction, then an additional hydrogen atom at $C_2$ is substituted by deuterium.

EXAMPLE II

Preparation of 1-ferrocenyl-2-aminopropane-1,2-$d_2$
(deuterated ferrocenyl propylamine)

Ferrocenyl-nitropropene is prepared by reacting 2.14 g ferrocenecarboxaldehyde with 2.25 g nitroethane 1.40 g ammoniumacetate and 10 ml of glacial acetic acid during 24 hours at room temperature in the dark. After heating the reaction mixture 2 hours at 100° C. and dilution with 100 ml of ice-water the formed ferrocenyl-nitropropene is extracted with diethylether. The organic solution is washed successively with $Na_2S_2O_4$-containing water, with diluted ammonia and finally with water until neutral. After drying and evaporating the diethylether, the residue obtained is recrystalized from methanol. The desired ferrocenyl-nitropropene is obtained in a yield of 80%; m.p. 48° C.; TLC: $R_f$(diethylamine/diethylether 5/95) 0.86.

The above-prepared ferrocenyl-nitropropene is dissolved in dry diethylether. To this solution upon cooling the sixfold molar amount of $LiAlD_4$ in dry diethylether is added slowly. The solution is refluxed during 2 hours, after which the excess of $LiAlD_4$ is inactivated by adding water drop-wise. Then the solution in diethylether is filtered, dried and the solvent is evaporated. Purification of the desired 1-ferrocenyl-2-aminopropane-1,2-$d_2$ is carried out as described for the corresponding ethylamine in Example I: yield 30%; melting point of the succinate 164° C. The compound is identified as Fc-CHD-CD($NH_2$)-$CH_3$ by mass spectrum and NMR spectrum: MS: m/e=245, 202, 165, 134, 121, 100, 85, 83, 74, 57 56, 46; $^1$H-NMR 250 MHz in $CDCl_3$: Fc-d=4.11 ppm; Fc-CHD-d=2.35 ppm D; -$CH_3$-d=1.03 ppm.

EXAMPLE III

In the same way as described in Example II 1-ferrocenyl-2-aminobutane-1,2-$d_2$ is prepared; m.p. of the succinate 136° C.; $^1$H-NMR 250 MHz in $CDCl_3$: Fc-$CH_2$-d=2.14 ppm; -$NH_2$-d=2.6 ppm; CH-d=1.42 ppm; $CH_2$-d=1.26 ppm; $CH_3$-d=0.92 ppm; MS: m/e=257, 240, 215, 200, 190, 149, 134, 121, 100, 74, 58, 56; TLC: $R_f$(acetone/ethanol/$NH_3$-aq.=95/5/2.5) 0.40.

EXAMPLE IV

The N-isopropyl derivatives of the compounds obtained according to Examples I-III are prepared as follows. The starting ferrocenyl-alkylamine in an amount of 9.0 mmol in a mixture of 12 mmol acetone, 2 g magnesium sulphate and 20 ml anhydrous methanol is converted with 9 mmol HCl (as 36% hydrochloric acid) and 6 mmol sodiumcyanoborohydride. After the reaction mixture has been stirred by room temperature during 72 hours the pH of the solution is adjusted at 2 with conc. HCl and the solvent is evaporated. Then the residue is dissolved in water and extracted frequently with diethylether. After making the mixture alkaline the free amine is extracted with diethylether and the organic solution is dried. Evaporation of the solvent yields the desired N-isopropyl derivative. The following deuterated compounds are obtained in this manner:

N-isopropyl-2-ferrocenyl-ethylamine-1,2-$d_2$: m.p. HCl-salt (recryst. from propanol/diethylether): 136° C. TLC: $R_f$(acetone/ethanol/$NH_3$-aq.=95/5/2.5) 0.58; $^1$H-NMR 250 MHz in $CDCl_3$: Fc-$C_2H_4$-d=3.07 ppm M; -NH-d=3.38 ppm; CH($CH_3$)$_2$-d=1.59 ppm; MS: m/e: 271, 256, 199, 147, 134, 121, 106, 72, 56.

N-isopropyl-1-ferrocenyl-2-aminopropane-1,2-$d_2$: m.p. succinate (recryst. from ethanol/diethylether): 148° C. TLC: $R_f$(acetone/ethanol/$NH_3$-aq.=95/5/2.5) 0.58. N-isopropyl-1-ferrocenyl-2-aminobutane-1,2-$d_2$: m.p. succinate: 130°-131° C.
TLC: $R_f$(diethylether/diethylamine=95/5) 0.68; MS: m/e: 299, 283, 270, 255, 240, 212, 200, 190, 186, 162 149, 134, 121, 100, 71.

EXAMPLE V

In the same way as described in Example IV N-isopropyl derivatives of the compounds obtained according to Examples I-III having 4 and 9 deuterium atoms in the molecule are prepared by using deuterated sodiumcyanoborohydride [Na(BCND$_3$)] instead of NaBCNH$_3$ as the reducing agent and both Na(BCND$_3$) and acetone-$d_6$ (instead of acetone) respectively. In this manner the following deuterated compounds are obtained:

N-(2'd-isopropyl)-1-ferrocenyl-2-aminopropane-1,2-$d_2$: $^1$H-NMR 250 MHz in $CDCl_3$: Fc-CH-d=2.41 ppm D; -$CH_3$-d=1.03 ppm S; -CD($CH_3$)$_2$-d=0.96 ppm.

N-(hepta-d-isopropyl)-1-ferrocenyl-2-aminopropane-1,2-$d_2$: MS: m/e: 294, 202, 121, 94, 93, 46.

EXAMPLE VI

The N-methyl derivatives of the compounds obtained according to Examples I-III are prepared as follows. The starting ferrocenyl-alkylamine is at first converted with benzaldehyde by heating equimolar amounts of both reactants in ethanol. After evaporating the solvent in vacuo the residue together with a threefold molar excess of methyliodide and a little anhydrous $Na_2CO_3$ is sealed in an ampoule and heated approx. 5 hours at 100° C. After cooling down to room temperature the content is washed out of the ampoule with a methanol/water=8/1 mixture and then refluxed for 0.5 hours to split off benzaldehyde. The warm solution is then poured into an equal volume of water and boiled until the smell of benzaldehyde has disappeared After cooling down the reaction mixture is made alkaline with 30% KOH-solution and extracted with diethylether. After drying the ether layer the solvent is evaporated in vacuo. The N-methyl derivative is purified by thin layer chromatography or by column chromatography (Al$_2$O$_3$; diethylether/diethylamine=95/5).

The N,N-dimethyl derivatives can be obtained in a corresponding manner by using a twofold molar amount of methyliodide; in this case a conversion with benzaldehyde is not necessary.

The following compounds are obtained:

N-methyl-1-ferrocenyl-2-aminopropane-1,2-$d_2$: TLC: $R_f$(diethylether/diethylamine=95/5) 0,29; $R_f$(ethanol-/acetone/$NH_3$-aq.=5/95/2.5) 0.26; $^1$H-NMR 250 MHz in $CDCl_3$: Fc-$CH_2$-d=2.47 ppm M; CH-d=2.69 ppm; $CH_3$-d=0.92 ppm; N-$CH_3$-d=2.33 ppm T; MS: m/e: 257, 242, 232, 229 200, 134, 121, 59, 45.

N,N-dimethyl-1-ferrocenyl-2-aminopropane-1,2-$d_2$: $^1$H-NMR 250 MHz in $CDCl_3$: Fc-$CH_2$-d=2.72 ppm Q; -CH-d=2.54 ppm M; -$CH_3$-d=0.82 ppm; N-($CH_3$)$_2$-d=2.33 ppm S; MS: m/e: 271, 257, 243, 226, 199, 134, 121, 72. TLC: $R_f$(diethylether/diethylamino=95/5) 0.47.

EXAMPLE VII

Preparation of $^{103}$Ru-labelled Ruthenocenyl-Alkylamines and Derivatives Thereof The above ferrocenyl compounds prepared according to Examples I-VI can be converted into the corresponding $^{103}$Ru-labelled ruthenocenyl compounds by exchanging the central metal atom as described hereinafter. Preferably, however, the N-methyl- and N, N-dimethyl-derivatives are prepared by at first converting the N-unsubstituted amines into the $^{103}$Ru-labelled ruthenocenyl alkylamines, followed by an N-methylation or N,N-dimethylation as described in Example VI.

By way of example the preparation of $^{103}$Ru-1-ruthenocenyl-2-aminopropane-1,2-$d_2$ and its N-methyl- and N,N-dimethyl derivatives are described hereafter:

1-Ferrocenyl-2-aminopropane-1,2-$d_2$ in an amount of 9 mg and approx. 65 μCi of $^{103}$RuCl$_3$ in a hydrochloric acid solution are brought into a glass ampoule. After evaporating the solvent, 0.15 ml of methanol containing 6% HCl is added, after which the glass ampoule is sealed under vacuum and subsequently heated at 120° C. during 1 hour. Thin layer chromatography with ethanol/acetone/NH$_3$-aq.=5/95/2.5 as the eluent yields the desired $^{103}$Ru labelled ruthenocenyl compound: R$_f$0.55; specific activity 0.48 μCi/μmol metallocene.

The above $^{103}$Ru-labelled ruthenocenyl compound is converted to the corresponding deuterated N-methyl- and N,N-dimethyl derivatives by adding $^{103}$Ru-1-ruthenocenyl-2-aminopropane-1,2-$d_2$ with the sevenfold molar amount of CDI$_3$ and 1 mg of anhydrous Na$_2$CO$_3$ into a glass ampoule while cooling in ice. After rinsing with 20 μl of dry toluene the cooled ampoule is sealed. After 4 hours heating at 100° C. the content of the ampoule is washed out of the ampoule with NH$_3$-aq.-containing methanol and chromatographed on a thin layer (diethylether/diethylamine=95/5). After elution with methanol/HCl the desired deuterated N-methyl- and N,N-dimethyl compounds are obtained having the respective formulas:

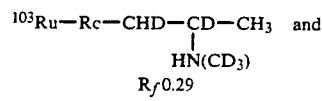

R$_f$0.29

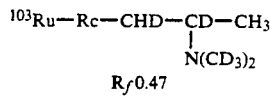

R$_f$0.47 wherein $^{103}$Ru-Rc means $^{103}$Ru-labelled ruthenocenyl.

EXAMPLE VIII

Preparation of Deuterated N-isopropyl-iodoamphetamine

While stirring 300 mg of para-iodophenylpropanone-2 is dissolved into 300 μg of isopropylamine. Then 155 mg of Na[BCND$_3$] and 30 mg of magnesium sulphate are added. After stirring at room temperature during 3 hours the reaction mixture is frequently eluted with methanol and purified by thin layer chromatography (silicagel; chloroform/acetone/formic acid=75/20/2.5). The fraction having a R$_f$value of 0.18 is isolated and eluted in methanol. The desired compound having the formula presented below is obtained in a yield of 254 mg. The deuteration at carbon atom 2 of the propane side chain can be confirmed by NMR The R$_f$-value is identical with that of the corresponding non-deuterated compound.

formula:

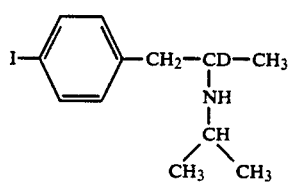

The above compound is converted to the corresponding iodine-131 compound with iodine-131 labelled sodium iodide under the influence of copper ions and ascorbic acid, exactly as described in European patent application 165630 e.g. Example I thereof.

EXAMPLE IX

Determination of the relaxation of the water protons by adding paramagnetic deuterated ferricinium compounds compared to the corresponding non-deuterated compounds. The following compounds are tested:
(a) $[(CH_3-C_5H_4)_2Fe]^+BF_4^-$
(b) $[(CH_3-C_5D_4)_2Fe]^+BF_4^-$
(c) $[(C_5H_5)_2Fe]^+BF_4^-$
(d) $[(C_5D_5)_2Fe]^+BF_4^-$ From the above compounds 2 millimolar solutions in water are prepared. Of these solutions the relaxation time $T_1$ is determined at 89.55 MHz on a JEOL FX-90Q NMR spectrometer using the inversion recovery method (room temp.). In the experiments comprising in addition deuterium oxide, $D_2O$ is added in a quantity of 1.0 mMole to a volume of 100 ml of the solution. The results are presented in Table A below.

TABLE A

| compound | $T_1$(sec.) |
|---|---|
| − (water blank) | 3.19 |
| (a) | 1.62 |
| (a) + $D_2O$ | 1.60 |
| (b) | 1.23 |
| − (water blank) | 3.44 |
| (c) | 1.65 |
| (c) + $D_2O$ | 1.64 |
| (d) | 1.04 |

The above results show that the deuterated compounds are more powerful paramagnetic water relaxing agents than their non-deuterated analogs, making them more suitable as NMR contrast agents. The observed enhancement in the relaxivity of the solutions of the deuterated complexes is not related to the nonspecific presence of deuterium (as $D_2O$) in the samples but is related to deuterium which is bonded to the complexes. When the relaxation time $T_2$ of the above solutions is determined, the same tendency is observed as for $T_1$.

EXAMPLE X

In vivo comparative experiments between $^{103}$Ru-labelled N-isopropyl ruthenocenyl-isopropylamine (N-isopropyl-ruthenocene-amphetamine) and the corresponding deuterated compound.

The above compounds are intravenously administered in doses of approx. 0.5 μmol/kg to two groups of each 4 rats. The compounds can be represented by the following formula:

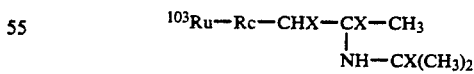

Rc = ruthenocenyl
X = H or D

After certain periods of time between 0 and 90 minutes after injection test animals are sacrificed and the $^{103}$Ru-concentration in the brains is determined. The results are graphically recorded in FIG. 1: the $^{103}$Ru-concentration (C) in the brains i.c. % dose/% body weight (% d/% wt), is plotted against the time (t) in min. The figure clearly demonstrates the increase in the brains of the $^{103}$Ru-labelled deuterated N-isopropyl-ruthenocene-amphetamine compared to the non-deuterated compound (control), viz. to 180% of the control values at most.

Figure 2:
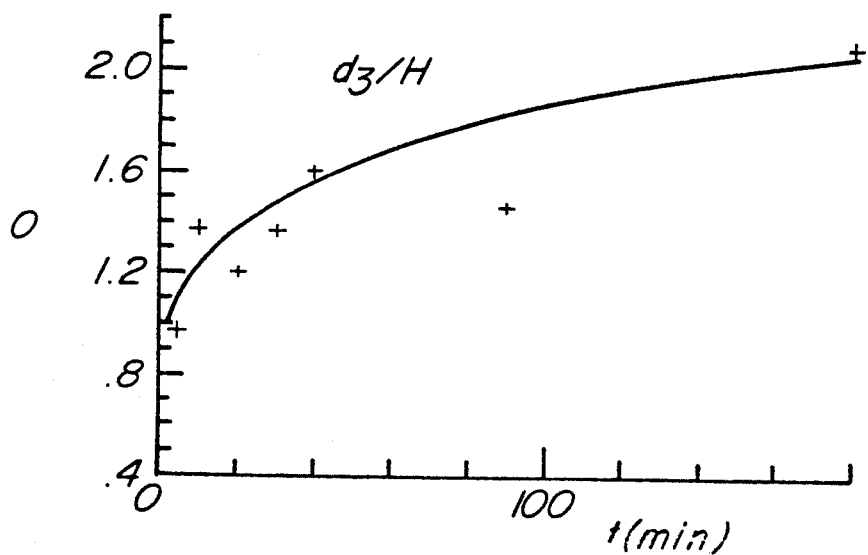

The same experiment is carried out in two groups of each 5 mice. In FIG. 2 the quotient (Q) of the $^{103}$Ru concentration of the deuterated compound and that of the non-deuterated compound (control) is plotted against the time (0–180 minutes). The $^{103}$Ru-concentrations in the brains for the deuterated compounds reach here values of up to 200% of the control values.

EXAMPLE XI

In the same way as described in Example X the effect of deuteration of N-methyl- and N,N-dimethylderivatives of $^{103}$Ru-labelled ruthenocene-amphetamine is investigated in vivo: groups of 3 or 4 rats as test animals; dose: 0.5 μmol/kg. After 15 or 20 minutes the $^{103}$Ru-concentration is determined in various organs of the rats, viz. brains, lungs and suprarenal glands, and presented in table B for the compounds tested. As will be apparent from the D/H value, i.e. the quotient of the $^{103}$Ru concentration of the deuterated compound and that of the non-deuterated compound, in all experiments except one (free amine-lungs) the affinity of the deuterated compounds to the organs is increased compared to the non-deuterated compounds. The decreased value for the free amine in the lungs cannot be explained.

TABLE B $^{103}$Ru-concentration in organs of rats after injection of Rc-amphetmine derivatives.
—NH$_2$ (free amine)$^{103}$Ru—Rc—CHX—CX(NH$_2$)—CH$_3$ X = H or D  —N-methyl —NH—CH$_3$ or —NH—CD$_3$
—N,N-dimethyl —N(CH$_3$)$_2$ or N(CD$_3$)$_2$

| compound | min. | 103Ru-concentration (% dosis/% body weight) | | | | | |
|---|---|---|---|---|---|---|---|
| | | brains | | lungs | | suprarenal glands | |
| | | D | H | D | H | D | H |
| —N-methyl | 15 | 2.56 | 2.28 | 11.3 | 9.0 | 8.3 | 4.7 |
| D/H | | 1.12 | | 1.26 | | 1.77 | |
| —N,N-dimethyl | 15 | 3.33 | 2.29 | 10.5 | 7.96 | 11.9 | 7.6 |
| D/H | | 1.45 | | 1.32 | | 1.57 | |
| —NH$_2$ | 20 | 2.56 | 1.95 | 10.5 | 12.3 | 6.2 | 4.8 |
| D/H | | 1.31 | | 0.85 | | 1.29 | |

EXAMPLE XII

Figure 3:
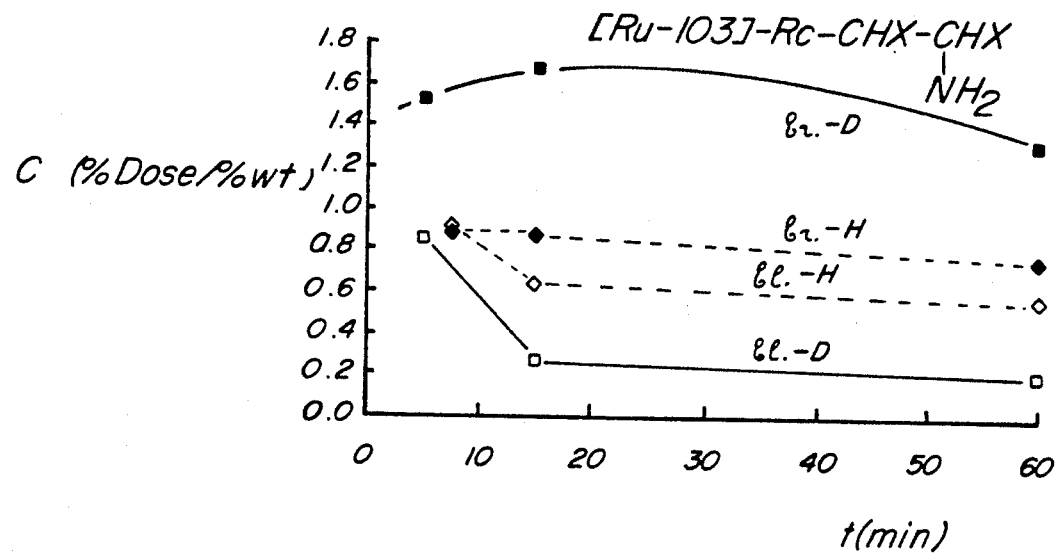

In the same way as described in Example X the effect of deuteration of $^{103}$Ru-labelled ruthenocenyl-ethylamine is investigated in rates; does: 0.3 μmol/kg. After 15 and 60 minutes the $^{103}$Ru-concentration is determined in the brains and in the blood of the test animals. The results are presented in FIG. 3; C[br-H] denotes the concentration of the non-deuterated compound in the brains, C[br-D] of the deuterated compound in the same organ, C[bl-H] and C[bl-D] denote the concentrations in the blood of the non-deuterated and deuterated compounds respectively. From the results it can be concluded, that the deuteration effects an increased uptake in the brains attended with a decreased uptake in the blood.

EXAMPLE XIII

Preparation of Deuterated N-isopropyl-haloamphetamine a) The conversion of p-bromobenzaldehyde with nitroethane is carried out by refluxing a solution of 50 mmol of the benzaldehyde with 150 mmol nitroethane and 6.9 g ammonium acetate in 50 ml glacial acetic acid at 100°–110° C. Upon cooling down to room temperature 4-bromophenyl nitropropane crystallizes and can be sucked off. The mother liquor is poured into appr. 0.5 l of ice-water and extracted which diethylether. The ether extract is successively washed with aqueous Na$_2$S$_2$O$_4$ solution, aqueous NH$_3$-solution and water until neutral dried and evaporated to dryness. The residue is crystallized from methanol and yields another portion of the desired 4-bromophenyl nitropropane. The combined crystalline material is washed with pentane and recrystallized from methanol: yield 52.4%; melting point 85°–88° C.

b) The above compound is reduced with LiAlD$_4$ by dissolving it in anhydrous diethylether and reduction with a threefold molar amount of LiAlD$_4$ when cooling in ice. After reflux during 2 hours at 37° C., excess of LiAlD$_4$ is discarded by adding water. After filtration the ether layer is dried and reduced to dryness. The desired 4-bromoamphetamine-d$_2$ ("bromo-d$_2$" below) is obtained as the HCl-salt with the aid of etheric HCl; yield 53%. TLC: R$_f$(ethanol-/acetone/NH$_3$=5:95:2.5)=0.54 MS: 216/218 m/e NMR: confirms the substitution of 2 H by 2 D at C$_1$ and C$_2$ of the propyl chain.

c) 4-Bromoamphetamine-d$_2$ in an amount of 2 mmol 1.33 mmol NaBD$_3$CN, 2 mmol CH$_3$COOD and 200 mg anhydrous MgSO$_4$ in 3 ml of anhydrous acetone is stirred during 2 hours at room temperature. After standing one day, centrifuging and extracting with warm acetone, the acetonic solution is evaporated to dryness. The residue is dissolved in diethylether and treated with etheric HCl, yielding the desired N-isopropyl-4-bromoamphetamine-d$_3$-HCl salt as a crystalline material: m.p. 150°–152° C.; yield 66%. TLC: R$_f$(diethylether/diethylamine=95:5)=0.58–0.60 MS: 259/261 m/e. NMR: confirms the substitution of 3 H by 3 D: "bromo-d$_3$" below.

d) Exactly as described in Example III c) N-isopropyl-4-bromoamphetamine-d$_9$ is prepared from 4-bromoamphetamine-d$_2$ and acetone-d$_6$: m.p. 150°–152° C.; yield 50.1%. confirms the substitution of 9 H by 9 D: "bromo-d$_9$" below.

e) In the same way as described in Example XIII c) N-isobutyl-4-bromoamphetamine-d$_2$ ("ibu-bromo-d$_2$") and N-isobutyl-4-bromoamphetamine-d$_3$ ("ibu-bromo-d$_3$") are prepared using NaBH$_3$CN and NaBD$_3$CN as reducing agents respectively, CH$_3$COOH instead of CH$_3$COOD and anhydrous methyl ethyl ketone instead of acetone.

ibu-bromo-d$_2$: Yield 61.6%; m.p. 146° C.; TLC: R$_f$(EtO/HNEt$_2$) = 95/5) = 0.63-0.64.
ibu-bromo-d$_3$: yield 88.7%; m.p. 144-145° C.;
    TLC: R$_f$(Et$_2$O/HNEt$_2$) = 95/5) = 0.63-0.64.
bromo-d$_2$: Br—Ph—CHD—CD(NH$_2$)—CH$_3$

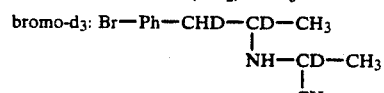

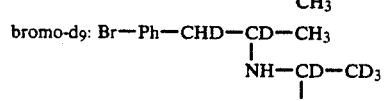

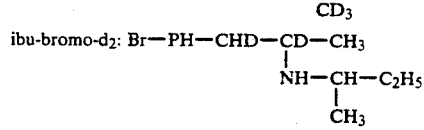

-continued

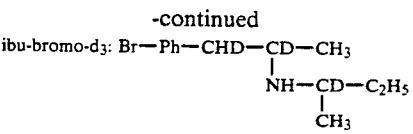

f) The above described bromine-substituted compounds are converted directly to the corresponding iodine-131 substituted compounds with iodine-131 in the form of carrier-free $^{131}I^-$; labelling conditions: 1 mg of bromine-substituted compound 5 mg of gentisic acid, 11 mg of citric acid, 0.2 mg of $SnSO_4$ and 25 $\mu l$ $Cu^{2+}$; solvent: approx. 500 $\mu l$ water. Heating in a closed vial at 140° C. for 120 minutes. The labelling efficiencies of the products obtained are determined by radio-HPLC and are substantially 100%, while no radioactive by products can be detected. The UV-chromatograms show that the starting bromo-compounds are completely absent. The corresponding iodine-123 substituted compounds are prepared in the same manner.

EXAMPLE XIV

Figure 4:
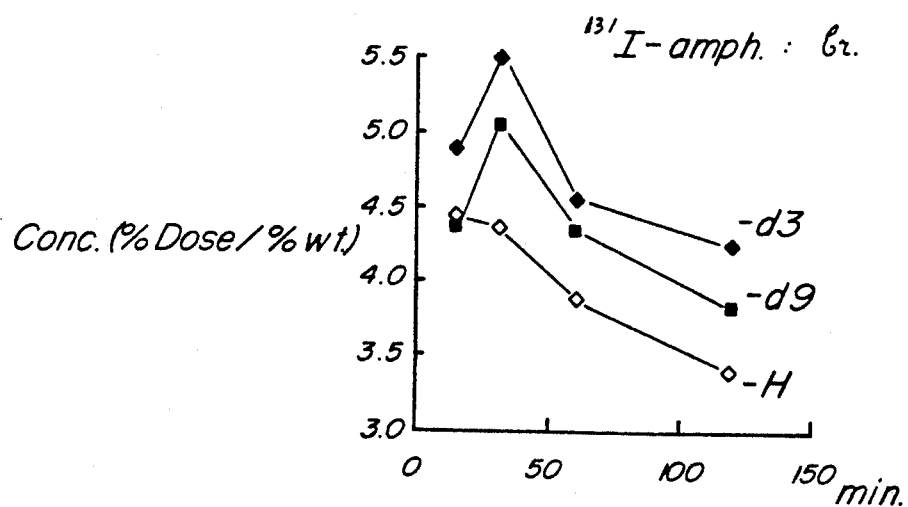
Figure 5:
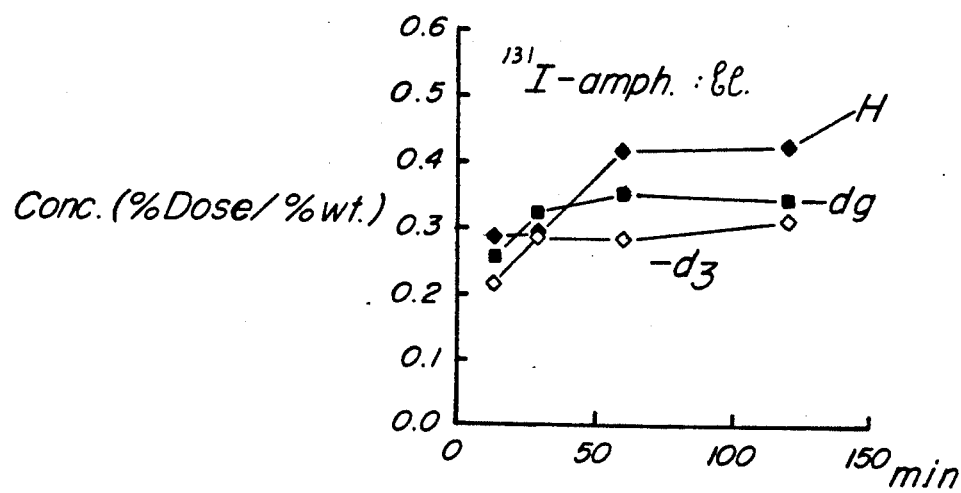
Figure 6:
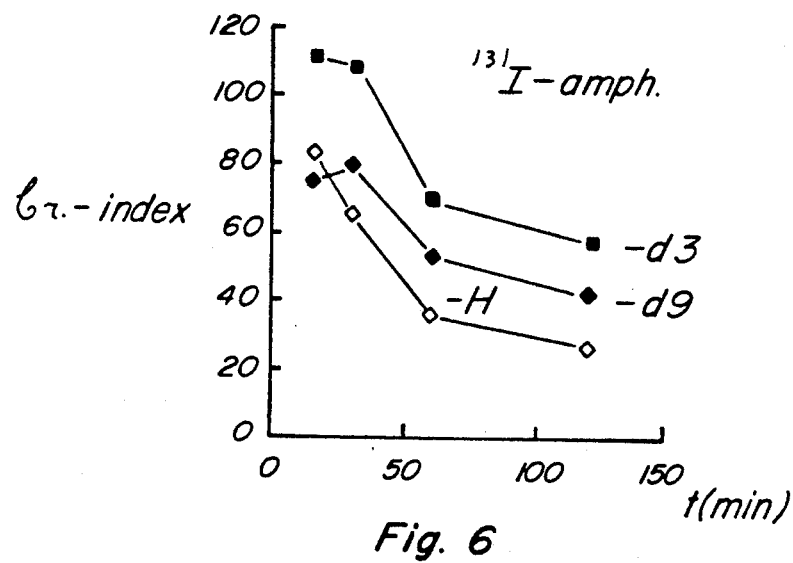

In the same way as described in Example X the effect of deuteration of I-131 labelled N-isopropyl-iodoamphetamine is investigated in vivo: groups of 4 rats as test animals; dose: 0.1 $\mu Ci/kg$; this corresponds with approx. $10^{-9}$ $\mu mol/kg$. After certain time-intervals the $^{131}I$-concentration is determined in the brains and in the blood of the test animals. The results are presented in FIGS. 4 and 5: in FIG. 4 the $^{131}I$-concentration in the brains is "H" is denoted the concentration of non-deuterated N-isopropyl-$^{131}I$-amphetamine, by "d$_3$" the concentration of N-isopropyl-$^{131}I$-amphetamine wherein 3H have been substituted by 3 D, and by "d$_9$" the concentration of N-isopropyl-$^{131}I$-amphetamine comprising 9 D. From the figures it will be clear that the deuteration effects an increased uptake in the brains attended with a decreased uptake in the blood, when the compounds are compared in the extremely low dosages required for diagnostic purposes. In FIG. 6 the above results are visualized by the so-called brains-index, calculated by dividing the squared brains-concentration by the blood-concentration. The deuterated compounds have a significantly favourable brains-index in comparison with the non-deuterated compound; the brains-index of the d$_3$-compound is most prominent.

EXAMPLE XV

Figure 7:
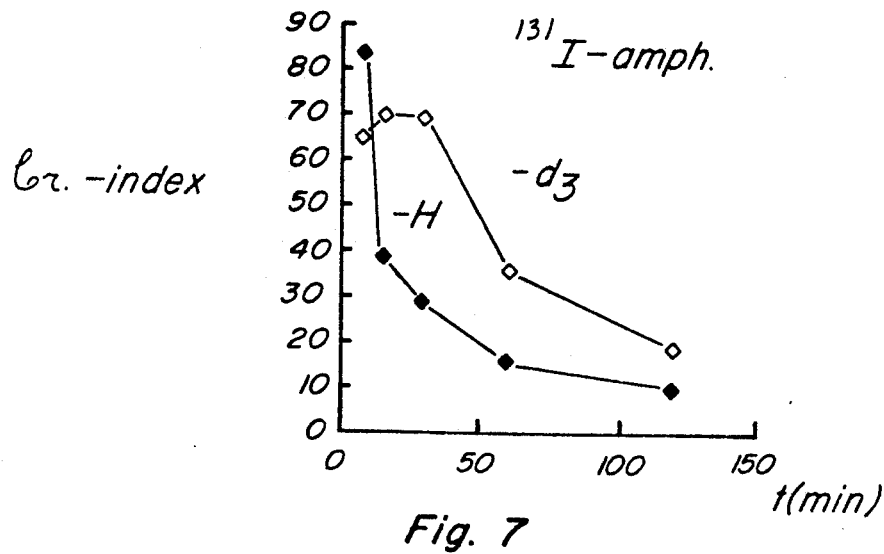

In exactly the same way as in Example XIV the non-deuterated N-isopropyl-$^{131}I$-amphetamine is compared with the corresponding 3 D compound ("d$_3$") in mice. The brains-index is presented in FIG. 7, showing that the d$_3$-compound has a significantly favourable brains-index compared with the non-deuterated compound.

EXAMPLE XVI

Preparation of t.-butylisocyanide-d$_9$ a) Preparation of N-t.-butylformamide-d$_9$ To a mixture of 15 g t.-butanol-d$_{10}$, 9.18 g 95% NaCN and 22.5 ml glacial acetic acid is added dropwise while stirring 44.5 g of conc. $H_2SO_4$ in 22.25 ml glacial acetic acid. Reaction temperature 50°-60° C. After 24 hours the reaction mixture is poured into 500 ml of water and neutralized with approx. 25% NaOH (upon cooling and stirring). N-t.-butylformamide-d$_9$ is extracted with diethylether, dried and evaporated: 12.9 g; b.p. 92°-94° C.

b) Preparation of t.-butylisocyanide-d$_9$

A solution of 10.78 g diphosgen in 55 ml -dichlorobenzene is added dropwise to a stirred and cooled (upon approx. $-14°$ C.) solution of 11.8 g t.-butylformamide-d$_9$, obtained as above under a). 23.17 g anhydrous triethylamine and 109 ml o-dichlorobenzene. After stirring for another 30 min. upon cooling and 2 hours at room temperature, 100 ml 0.15M phoshate buffer of pH 5 is added slowly. The organic phase is separated from the aqueous phase and, after shaking with 0.5N NaOH, dried on $K_2CO_3$. The desired product is distilled from the solvent o-dichlorobenzene at ambient pressure. The fraction distilling under 140° C. is purified by fractional distillation. t.-Butylisocyanide-d$_9$ is obtained in a yield of 6.52 g; b.p. 89°-90° C. NMR shows that t.-butylisocyanide is deuterated for 82%.

c) The t.-butylisocyanide-d$_9$ can be used in a kit formulation and labelled with technetium-99m as follows. A solution of 1 mg t.-butylisocyanide-d$_9$ in 1 ml ethanol is added to 5 mg of $Na_2S_2O_4$ in 0.25 ml water, and, after addition of 1 ml of eluate of a technetium generator, comprising 60 mCi of Tc-99m in the form of pertechnetate, heated on a boiling water bath during 10 min. The conversion is analysed by HPLC, using Zorbax RP6 as the carrier medium and 0.05M $(NH_4)_2SO_4$ in methanol as the solvent. The Tc-99m radiolabelled t.-butylisocyanide-d$_9$ is then compared with the corresponding non-deuterated compound by administering 1 ml thereof intravenously to a baboon. After 60 minutes the radioactivity in the heart is determined. The radioactivity in the heart of the baboon for the deuterated compound is approx. 7% higher than for the non-deuterated compound.

EXAMPLE XVII

In the same way as described by Wieland et al in J. Med. Chem. 1984, 27, 149-155, I-131 labelled deuterated m-iodobenzylguanidine is prepared from m-iodophenylmethylamine-d$_2$. Said deuterated m-iodobenzylamine is prepared by reduction of the corresponding nitrile (or acid amide, if desired) with $LiAlD_4$. The corresponding m-iodophenylethylamine-d$_2$ is prepared from m-iodobenzaldehyde and nitromethane as described in Example XIII a); this compound is converted to the radiolabelled deuterated guanidine derivative as described above and can then be used for radiotherapy of tumours.

I claim:

1. A radiodiagnostic or radiotherapeutic composition, comprising a radiolabelled hydrogen containing compound which has been labelled with a diagnostic or therapeutic radionuclide, and a pharmaceutically acceptable liquid, wherein the radiolabelled hydrogen containing compound includes at least one deuterium atom.

2. A diagnostic composition as claimed in claim 1, wherein the hydrogen containing compound is an NMR contrast agent selected from the group consisting of metal complexes of unsubstituted or substituted cyclopentadienyl and metals of the 7th or 8th subgroup or their derivatives or salts, metal chelates of $C_2$-$C_5$ alkylene di- or polyamineacetic acids and lanthanides or their salts, nitroxyles, and aminoxides, characterized in that the NMR contrast agent comprises at least one deuterium atom.

3. A composition as claimed in claim 2, characterized in that the NMR contrast agent is a substance selected from the group consisting of (a) a ferricinium compound that is unsubstituted or substituted with at least one side chain group, selected from $C_1$–$C_4$ alkyl, $C_1$–$C_4$ alkoxy and $C_2$–$C_5$ alkoxycarbonyl, wherein at least one hydrogen atom of the ferrocene ring system and/or at least one hydrogen atom of the side chain group, if present, is substituted by deuterium, and (b) a chelate of gadolinium or its salt and a $C_2$–$C_5$ alkylene di or polyamineacetic acid of which at least one C—H bond is substituted by a C—D bond.

4. A radiotherapeutic composition as claimed in claim 1, wherein the hydrogen containing compound, which is a high-molecular compound, preferably selected from the group consisting of proteins and proteinaceous substances, or a low-molecular compound, preferably selected from the group consisting of guanidine derivatives, bleomycine and aliphatic phosphonates, carries a radionuclide suitable for radiotherapy, preferably selected from the group consisting of I-131, Re-186, Re-188, Cu-67, Pb-212, Bi-212, As-77, Y-90, Ag-111 and Pd-109, characterized in that the hydrogen containing compound comprises at least one deuterium atom.

5. A diagnostic composition as claimed in claim 1, wherein the radiolabelled hydrogen containing compound is a radiolabelled compound selected from the group consisting of radiolabelled N-alkylaminoalkylaryl compounds, radiolabelled matallocenyl compounds, radiolabelled fatty acids, radiolabelled carbohydrates, radiolabelled proteins or proteinaceous substances, radiolabelled peptides selected from the group consisting of amino acids, di-, tri- or polypeptides, metal-radionuclides chelated with alkyleneamine oximes, metal-radionuclides chelated with substituted or unsubstituted alkyl isocyanides and boronic acid adducts of metal-rationuclides chelated with oximes, wherein the radiolabel is selected from radioactive halogen or from a metal-radionuclide, and wherein the metal-radionuclide is selected from the group consisting of TC-99m, Pb-203, Ga-67, Ga-68, As-72, In-111, In-113m, Ru-95 and Ru-97, characterized in that the radiolabelled compound includes at least one deuterium atom.

6. A composition as claimed in claim 5, characterized in that the radiolabelled compound is a compound of the general formula

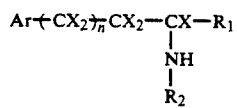

wherein

Ar is a radioactive halogen-labelled phenyl group or a metallocenoyl group radiolabelled with ruthenium 95 or ruthenium 97, $R_1$ is a hydrogen atom or a $C_1$–$C_4$ alkyl group $R_2$ is a $C_1$–$C_6$ alkyl group of which the hydrogen atom or atoms may be deuterated, X is completely or partly deuterated hydrogen, and n is 0 or 1.

7. A method of subjecting a warm-blooded living being to a radioassay, comprising the steps of:
  (a) obtaining a radiopharmaceutical formulation comprising a composition as claimed in claim 5 or 6, and a pharmaceutically acceptable liquid,
  (b) administering a diagnostically effective amount of the radiopharmaceutical formulation to the warm-blooded living being, and
  (c) imaging the warm-blooded living being to detect and locate accumulated radioactivity in the body of the being.

8. A kit for preparing a radiodiagnostic composition comprising:
  a non-radiolabelled deuterated compound selected from the group consisting of deuterated N-alkylaminoalkylaryl compounds, deuterated metallocenyl compounds, deuterated fatty acids, deuterated carbohydrates, deuterated proteins or proteinaceous substances, deuterated peptides selected from the group consisting of amino acids, di-, tri- or polypeptides, deuterated alkyleneamine oximes, substituted or unsubstituted deuterated alkyl isocyanides, and deuterated oximes, said non-radiolabelled deuterated compound being capable of reacting with a radiolabelling agent selected from the group consisting of water soluble compounds of a radioactive halogen, metal-radionuclide salts, and chelates of metal-radionuclides, wherein the metal radionuclide is selected from the group consisting of Tc-99m, Pb-203, Ga-67, Ga-68, As-72, In-111, In-113m, Ru-95, and Ru-97,
  one or more formulation agents to which a solution of the desired radionuclide should be added, and
  instructions for reacting the non-radiolabelled deuterated compound with the radiolabelling agent.

9. A kit as claimed in claim 8, wherein the non-radiolabelled deuterated compound is a deuterated $C_2$–$C_8$ alkyl isocyanide, preferably deuterated t.-butylisocyanide.

10. A method of subjecting a warm-blooded living being to a radioassay as defined in claim 7, wherein the quantity of radiopharmaceutical formulation administered to the living being is in the range from about 0.1 to about 10 millicurie per 70 kg of body weight.

11. A kit for preparing a radiodiagnostic composition as defined in claim 8, further comprising a reducing agent.

* * * * *